(12) United States Patent
Wilkinson (10) Patent No.: US 7,258,678 B2
(45) Date of Patent: Aug. 21, 2007

(54) RETRACTABLE SAFETY NEEDLE

(75) Inventor: Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 791 days.

(21) Appl. No.: 10/384,896

(22) Filed: Mar. 7, 2003

(65) Prior Publication Data

US 2003/0176843 A1    Sep. 18, 2003

Related U.S. Application Data (60) Provisional application No. 60/364,384, filed on Mar. 14, 2002.

(51) Int. Cl.
*A61M 5/00*    (2006.01)

(52) U.S. Cl. ..................................... 604/110

(58) Field of Classification Search ............... 604/110, 604/199, 86, 162, 164.08, 171, 201, 264, 604/268, 272; 128/919
See application file for complete search history.

(56) References Cited

U.S. PATENT DOCUMENTS

| | | | |
|---|---|---|---|
| 4,592,744 A | 6/1986 | Jagger et al. |
| 4,731,059 A | 3/1988 | Wanderer et al. |
| 4,747,831 A | 5/1988 | Kulli |
| 4,838,869 A | 6/1989 | Allard |
| 4,846,808 A | 7/1989 | Haber et al. |
| 4,871,355 A | 10/1989 | Kikkawa |
| 4,900,307 A | 2/1990 | Kulli |
| 4,917,673 A | 4/1990 | Coplin |
| 4,927,414 A | 5/1990 | Kulli |
| 4,942,881 A | 7/1990 | Al-Sioufi et al. |
| 4,991,601 A | 2/1991 | Kasai et al. |
| 4,993,426 A | 2/1991 | Spencer |
| 4,994,034 A | 2/1991 | Botich et al. |
| 5,030,209 A | 7/1991 | Wanderer et al. |
| 5,062,837 A | 11/1991 | Al-Sioufi et al. |
| 5,069,225 A | 12/1991 | Okamura |
| 5,120,311 A | 6/1992 | Sagstetter et al. |
| 5,143,083 A | 9/1992 | Al-Sioufi et al. |
| 5,188,599 A | 2/1993 | Botich et al. |
| 5,217,025 A | 6/1993 | Okamura |
| 5,219,333 A | 6/1993 | Sagstetter et al. |
| 5,407,431 A | 4/1995 | Botich et al. |

(Continued)

FOREIGN PATENT DOCUMENTS

WO    WO 99/23947    5/1999

(Continued)

*Primary Examiner*—Manuel Mendez
(74) *Attorney, Agent, or Firm*—Mark Lindsey (57) ABSTRACT

A retractable safety needle apparatus is provided. The apparatus includes a needle holder with opposite proximal and distal ends. A needle assembly is mounted in the needle holder for movement from a first position where a distal cannula projects distally beyond the needle holder and a second position where the distal cannula is entirely within the needle holder. A spring is provided for propelling the needle assembly proximally and into the second position. The needle assembly includes a deflectable actuator for releasably holding the needle assembly in the first position and against the biasing forces of the spring. Portions of the needle holder adjacent the distal end are tapered to facilitate alignment of the needle assembly and to provide visual cues for proper orientation and gripping locations.

19 Claims, 8 Drawing Sheets

U.S. PATENT DOCUMENTS

| | | |
|---|---|---|
| 5,591,138 A | 1/1997 | Vaillancourt |
| 5,693,028 A | 12/1997 | Shillington |
| 5,755,673 A | 5/1998 | Kinsey |
| 5,788,677 A | 8/1998 | Botich et al. |
| 5,797,490 A | 8/1998 | Fujii et al. |
| 5,800,395 A | 9/1998 | Botich et al. |
| 5,810,775 A | 9/1998 | Shaw |
| 6,004,278 A | 12/1999 | Botich et al. |
| 6,024,727 A | 2/2000 | Thorne et al. |
| 6,039,713 A | 3/2000 | Botich et al. |
| 6,074,373 A | 6/2000 | Sudo et al. |
| 6,077,244 A | 6/2000 | Botich et al. |
| 6,123,688 A | 9/2000 | Botich et al. |
| 6,179,812 B1 | 1/2001 | Botich et al. |
| 6,302,868 B1 | 10/2001 | Mohammad |
| 6,524,276 B1 | 2/2003 | Halseth et al. |
| 2002/0004648 A1 | 1/2002 | Larsen et al. |

FOREIGN PATENT DOCUMENTS

| | | |
|---|---|---|
| WO | WO 99/44660 | 9/1999 |
| WO | WO 99/47194 | 9/1999 |
| WO | WO 00/06221 | 2/2000 |
| WO | WO 00/12160 | 3/2000 |
| WO | WO 00/27450 | 5/2000 |
| WO | WO 00/35367 | 6/2000 |
| WO | WO 01/45776 | 6/2001 |
| WO | WO 01/66179 | 9/2001 |
| WO | WO 01/78595 | 10/2001 |
| WO | WO 01/93924 | 12/2001 |
| WO | WO 03/015855 A1 | 2/2003 |

RETRACTABLE SAFETY NEEDLE

RELATED APPLICATIONS

This application is a non-provisional of U.S. Provisional Patent Appl. No. 60/364,384, filed Mar. 14, 2002.

FIELD OF THE INVENTION

The invention relates to a retractable safety needle, and more particularly to a retractable safety needle mounted to a needle holder that is intended for use with an evacuated fluid collection tube.

BACKGROUND OF THE INVENTION

Many medical procedures require samples of bodily fluid, such as blood, to be collected and analyzed. The samples often are collected in an evacuated tube that has a cylindrical side wall, a closed bottom and an open top. The open top is closed by a needle pierceable and resealable material. Evacuated tubes of this general type are sold by Becton Dickinson under the trademark VACUTAINER®.

Evacuated tubes typically are employed with a needle assembly and a needle holder. The needle holder typically includes a rigid cylindrical side wall with proximal and distal ends. The proximal end of the side wall is widely open and is dimensioned for slidable receipt of the evacuated tube. A distal end wall extends across the distal end of the tubular side wall, and includes an aperture for engaging the needle assembly.

The typical needle assembly includes a plastic hub configured to mount in the aperture through the distal end wall of the needle holder. The needle assembly further includes a proximal needle cannula extending proximally from the hub and a distal needle cannula extending distally from the hub. Safety shields are mounted releasably to the needle hub for covering both the proximal and distal needle cannulas prior to use.

The needle holder and needle assembly are employed by first removing the safety shield from the proximal needle and mounting the needle hub in the aperture of the distal end wall of the needle holder. Thus, the proximal needle projects into the needle holder. The distal safety shield then may be removed and the distal needle cannula may be urged into a blood vessel or other source of bodily fluid. Typically the health care worker will align the needle holder so that the bevel at the distal end of the distal needle cannula faces up. Thus the health care worker will have to rotate the cylindrical needle holder by hand to achieve the preferred bevel orientation. Additionally, the health care worker will want as small an angle of entry of needle cannula into the patient as is permitted by the geometry of the needle holder.

An evacuated tube can be inserted into the open proximal end of the needle holder after the blood vessel or other source of bodily fluid has been accessed. Movement of the evacuated tube into the needle holder urges the proximal needle cannula into the evacuated tube and places the low pressure interior of the evacuated tube in communication with the source of bodily fluid. Hence, a flow of the bodily fluid is generated into the evacuated tube. The evacuated tube is separated from the needle holder after a sufficient volume of the fluid has been collected. Additional evacuated tubes can be urged sequentially into the needle holder to collect additional samples.

The needle holder and needle assembly are withdrawn from the patient after a sufficient number of fluid samples have been collected. The distal needle cannula then is shielded to prevent accidental sticks, and the shielded assembly is discarded in a sharps receptacle.

Many different shielding mechanisms are commercially available. Accordingly, there is a potential for improper shielding of a used needle cannula due to a lack of familiarity with the particular shield. A demand exists for a shieldable medical implement with an easy and efficient shielding mechanism and with visual and tactile cues to ensure that shielding is carried out efficiently and correctly.

SUMMARY OF THE INVENTION

The invention is directed to a retractable safety needle apparatus that comprises a needle holder, a needle assembly and a spring. The needle holder is an elongate structure with a widely open proximal end and a distal end. A generally tubular side wall extends from the proximal end to the distal end, and a distal end wall extends inwardly at the distal end. The distal end wall has a needle aperture for receiving a portion of the needle assembly.

Proximal portions of the tubular side wall may be substantially cylindrical. However, distal portions of the tubular side wall are non-cylindrical and comprise top and bottom panels that taper toward one another. The taper of the bottom panel facilitates a flat, small angle entry of the needle cannula into the patient. The taper of the top panel facilitates observation of the needle cannula and provides a visual alignment cue for the health care worker. The distal end of the tubular side wall also has recessed side panels. The side panels may be provided with a non-smooth surface to facilitate gripping and digital manipulation by a thumb and forefinger of the healthcare worker.

Proximal portions of the needle holder include an outwardly extending non-circular flange with a major axis extending in a side-to-side direction and a minor axis extending in a top to bottom direction. The non-circular configuration of the flange provides another visual cue for the preferred orientation of the needle holder. Additionally, the non-circular configuration of the flange prevents the needle holder from rolling on a flat surface.

The tubular side wall of the needle holder includes an actuating aperture at a location symmetrical with the top panel. An outwardly convex channel may extend from the actuating aperture to the flange at the proximal end of the needle holder.

The needle assembly includes a plastic hub with opposite proximal and distal ends and a passage extending between the ends. The proximal end of the needle hub may include an array of external threads.

The needle assembly further includes proximal and distal needle cannulas secured in the passage of the needle hub. Each cannula has a lumen and the lumens communicate with one another. Additionally, the end of each cannula remote from the hub is beveled to a sharp point. An elastic needle-pierceable sleeve is mounted over the proximal needle and is secured to the needle hub in a known manner.

The needle assembly also includes a needle platform that telescopes non-rotatably within the needle holder. The needle platform has proximal and distal ends and a passage extending between the ends. Distal portions of the passage include an array of internal threads for engaging the external threads on the needle hub.

An actuator is cantilevered proximally from the needle platform. The free end of the cantilevered actuator defines an actuator button that is dimensioned to project through the actuating aperture in the tubular side wall of the needle holder. Outwardly facing surface regions of the actuator button preferably are non-smooth and may include at least one bump or other surface configuration to facilitate tactile detection and actuation and to provide a further visual cue for the user. Additionally, the actuator button faces in the same direction as the bevel at the tip of the distal needle cannula.

The needle assembly may further include a safety shield telescoped over the distal needle and frictionally mounted on distal portions of the needle hub. Proximal portions of the safety shield may be dimensioned to telescope slightly into the central aperture in the distal end wall of the needle holder.

The spring of the retractable safety needle has a proximal end engaged with the needle platform and a distal end engaged with interior portions of the distal end wall of the needle holder.

The retractable safety needle assembly is used by gripping the opposed recessed side panels of the needle holder with a thumb and forefingers. Gripping may be facilitated by a non-smooth exterior surface of the side panels. Bumps, recesses or dots with a different surface texture may provide a further visual cue for the proper gripping areas. The user then pulls the safety shield distally relative to the needle holder to expose the distal needle cannula. The bevel of the distal needle cannula is oriented upwardly when the needle holder is gripped by the recessed side panels. The pointed distal end of the needle cannula then can be aligned with and penetrated into a selected blood vessel or other source of fluid. This alignment and targeting of the distal needle cannula is facilitated by the upward alignment of the bevel and by the tapered top and bottom panels of the needle holder. A substantially flat entry also is facilitated by the tapered bottom panel.

An evacuated tube can be urged into the open proximal end of the needle holder after the targeted source of bodily fluid has been accessed. The seal across the evacuated tube is pierced by the proximal needle to place the evacuated tube into communication with the bodily fluid. As a result, a flow of bodily fluid is generated into the evacuated tube. One or more evacuated tubes may be filled in the same manner. The needle then is withdrawn from the patient by pulling proximally on the needle holder. The health care worker then depresses the actuator button with the index finger of the hand that grips the needle holder to release the actuator from the side wall. As a result, the spring propels the needle assembly proximally a sufficient distance for the pointed distal end of the distal needle cannula to be safely enclosed within the tubular side wall of the needle holder.

DETAILED DESCRIPTION OF THE INVENTION

A retractable safety needle apparatus in accordance with the subject invention is identified generally by the numeral 10 in FIGS. 1-7. Retractable safety needle apparatus 10 includes a needle holder assembled from an outer holder 12 and an inner holder 4. Outer holder 12 is unitarily molded from a rigid plastic material and includes a widely open proximal end 16 and a partly closed distal end 18. A generally tubular side wall 20 extends between proximal and distal ends 16 and 18. A distal end wall 22 extends radially inwardly from side wall 20 at distal end 18 and is characterized by a central aperture 24. Aperture 24 is dimensioned to receive portions of a needle assembly, as explained further below.

Outer holder 12 is configured to provide visual cues for a preferred rotational orientation and a preferred method of usage. More particular, side wall 20 includes a substantially cylindrical portion 26 adjacent proximal end 16 of outer holder 12. However, portions of side wall 20 adjacent distal end 18 defines a non-cylindrical configuration with tapered top and bottom panels 28 and 30 and recessed side panels 32 and 34. Top and bottom panels 28 and 30 are tapered respectively from top and bottom boundaries 36 and 38 with cylindrical portion 26. Boundaries 36 and 38 lie on a common radially aligned plane, as shown most clearly in FIG. 4. Top and bottom panels 28 and 30 exhibit a side-to-side convexity that is flatter than the convexity existing on cylindrical portion 26 of side wall 20.

Side panels 32 and 34 are recessed inwardly relative to cylindrical portion 26 of side wall 20, and extend distally from side boundaries 40 and 42, which are adjacent cylindrical portion 26 of side wall 20. Side boundaries 40 and 42 are curved generally parabolically and extend proximally from top and bottom boundaries 36 and 38. Thus side panels 32 and 34 extend proximally beyond top and bottom panels 28 and 30. Outer surfaces of side panels 32 and 34 are characterized by a linear array of bumps 44 that provides a visual cue for a proper gripping location and that facilitate gripping of side surfaces 32 and 34 by a thumb and forefinger.

Cylindrical portion 26 of side wall 20 is characterized by a channel 46 that extends longitudinally from a central position on top panel 28 to proximal end 16 of needle holder 12. Channel 46 has a convex outer surface and a concave inner surface. The distal end of channel 46 is characterized by an actuating aperture 48 adjacent boundary 36 of top surface 28. Actuating aperture 48 defines a distal point which functions as a further visual cue for proper alignment and orientation of outer holder 12.

Proximal end 16 of outer holder 12 is characterized by outwardly extending flange 50. Flange 50 is non-circular, and defines a major axis extending in a side-to-side direction and a minor axis extending in a top to bottom direction. Flange 50 also has a concave edge 51 aligned symmetrically with bottom panel 30 and a convex protrusion 52 aligned with channel 46. The non-circular configuration of flange 50 prevents retractable safety needle assembly 10 from rolling on a planar surface, and provides visual cues for the proper top-bottom orientation.

Inner holder 14 also is unitarily formed from a rigid plastic material and includes a proximal end 53, a distal end 54 and an inner circumferential surface 56 extending distally from proximal end 53. Inner holder 14 is dimensioned to be telescoped within outer holder 12 and can be locked in a position where proximal end 53 of inner holder 14 substantially aligns with proximal end 16 of outer holder 12. Inner circumferential surface 56 of inner holder 14 is dimensioned to slidably receive an evacuated tube (not shown). A channel 58 is formed in a top portion of inner holder 14. Channel 58 is open at distal end 54 of inner holder 14. However, a stop projection 60 closes channel 58 at locations substantially adjacent proximal end 53 of inner holder 14.

Retractable safety needle apparatus 10 further includes a needle assembly 62. Needle assembly 62 includes a unitarily molded plastic hub 64 with opposite proximal and distal ends 66 and 68 and a passage extending between the ends. External thread 70 are formed on hub 64 adjacent proximal end 66.

Needle assembly 62 also includes a proximal needle cannula 72 with a distal end securely mounted in hub 64 and a proximal end 74. A needle pierceable elastic sleeve 75 is telescoped over proximal needle cannula 72 and is mounted adjacent proximal end 66 of needle hub 64. Needle assembly 62 further includes a distal needle cannula 76 with a proximal end mounted in proximal end 68 of needle hub 64 and a sharply beveled distal end 78. Distal needle cannula 76 further includes a lumen 79 that communicates with the lumen (not shown) through proximal needle 72.

Needle assembly 62 further includes a generally tubular needle platform 80. Needle platform 80 includes a proximal end 82, a distal end 84 and a passage 86 extending therebetween. Portions of passage 86 adjacent distal end 84 define an array of internal threads that are dimensioned and configured for receiving external threads 70 on needle hub 64. Needle platform 80 is cross-sectionally larger than aperture 24 in distal end wall 22 of outer holder 12. As a result, distal end wall 22 defines a limit on distal movement of needle assembly 62 in the needle holder.

An actuator 88 is unitary with needle platform 80 and is cantilevered proximally from proximal end 82 of needle platform 80. An actuator button 90 projects radially out from proximal end of actuator 88. Actuator button 90 has a shape corresponding to actuating aperture 48 in front holder 12. More particularly, actuator button 90 includes a distally directed pointed end that can nest in the pointed distal end of actuating aperture 34. Actuating button 90 is further characterized by a bump 92 on the radial outer surface. Bump 92 provides both a visual and tactile indication of an approximate point at which digital forces may be exerted on actuator button 90.

Needle assembly 62 further includes a safety shield 94. Safety shield 94 includes a rigid tubular side wall 96, an open proximal end 98 and a closed distal end 100. Portions of safety shield 94 adjacent proximal end 98 define an inside diameter approximately equal to the outside cross-sectional dimensions defined by distal end 68 of hub 64. Additionally, portions of safety shield 94 adjacent proximal end 98 define an external diameter approximately equal to or slightly less than the diameter of aperture 24 in distal end wall 22 of outer holder 12.

Retractable safety needle apparatus 10 further includes a coil spring 102 with a proximal end 104 and a distal end 106. Proximal end 104 of coil spring 102 is telescoped over and trapped by needle platform 80. Distal end 106 of spring 102 is engaged against the inner surface of distal end wall 22 on outer holder 12.

Retractable safety needle apparatus 10 is assembled by threading hub 64 into passage 86 of needle platform 80 so that pointed proximal end 74 of proximal needle cannula 72 and its sleeve 75 project proximally beyond needle platform 80. Additionally, the threaded connection of hub 64 and needle platform 80 will cause actuator button 90 and bevel 78 of distal needle cannula 76 to be symmetrical about a common plane and to face substantially in the same direction. Spring 102 then is telescoped into open proximal end 16 of outer holder 12 and needle assembly 62 is telescoped through spring 102 and through aperture 24 in distal end wall 22 of outer holder 12. More particularly, cantilevered actuator arm 88 is slidably received in channel 46 in a slightly inwardly deflected condition. Distal advancement of needle assembly 62 into outer holder 12 causes spring 102 to collapse. After sufficient distal movement, actuating button 90 will align with actuator aperture 34. As a result, cantilevered arm 88 will resiliently move outwardly so that actuating button 90 is releasably engaged in actuating aperture 48. Inner holder 14 then is advanced distally into open proximal end 16 of outer holder 12. Inner holder 14 will lock with outer holder 12 when proximal end 53 of inner holder 14 aligns with proximal end 16 of outer holder 12. Safety shield 94 then is telescoped over distal needle cannula 76 so that interior portions of safety shield 94 adjacent proximal end 98 are frictionally engaged on needle hub 64 to complete the assembly.

Retractable safety needle apparatus 10 is used by grasping outer holder 12 with a thumb and forefingers at recessed side panels 32 and 34 such that top panel 28 and actuator button 90 face upwardly. Concave recess 51 and convex protrusion 52 on flange 50 cooperate with the convex outer surface of channel 46 to provide clear visual cues for the proper "up" orientation. The health care worker then grips safety shield 94 and exerts a sufficient distal pulling force to separate safety shield 94 from needle hub 64. Beveled distal tip 78 of distal needle cannula 76 will be facing upwardly and in the same direction as both tapered top panel 28 of outer shield 12 and actuator button 90. The health care worker then can place beveled distal tip 78 of distal cannula 76 into communication with a blood vessel or other source of bodily fluid that is to be collected. The tapered bottom panel 30 of outer holder 12 adjacent distal end 18 facilitates a flat small angle approach of distal needle cannula 76 to the patient. Additionally, pointed end of actuator button 90 and the generally parabolic configuration of side boundaries 40 and 42 of side surfaces 32 and 34 provide visual cues for appropriate orientation and alignment of needle assembly 10.

Fluid samples are collected with needle apparatus 10 in a conventional manner by inserting evacuated tubes into open proximal end 53 of inner holder 14. Actuator button 90 may be depressed by the index finger of the hand that grips recessed side panels 32 and 34 after a sufficient number of fluid specimens have been collected and removed from needle holder. Inwardly directed digital forces on actuator button 90 cause cantilevered actuator arm 88 to deflect inwardly for separating actuator button 90 from the periphery of actuating aperture 48. This release of actuator button 90 from actuating aperture 48 effectively releases needle assembly 62 and permits spring 102 to propel needle assembly 62 proximally a sufficient distance for pointed distal end 78 of distal cannula 76 to be shielded safely within outer shield 12. The health care worker then deposits retractable safety needle assembly 10 in a sharps receptacle.

Figure 1:
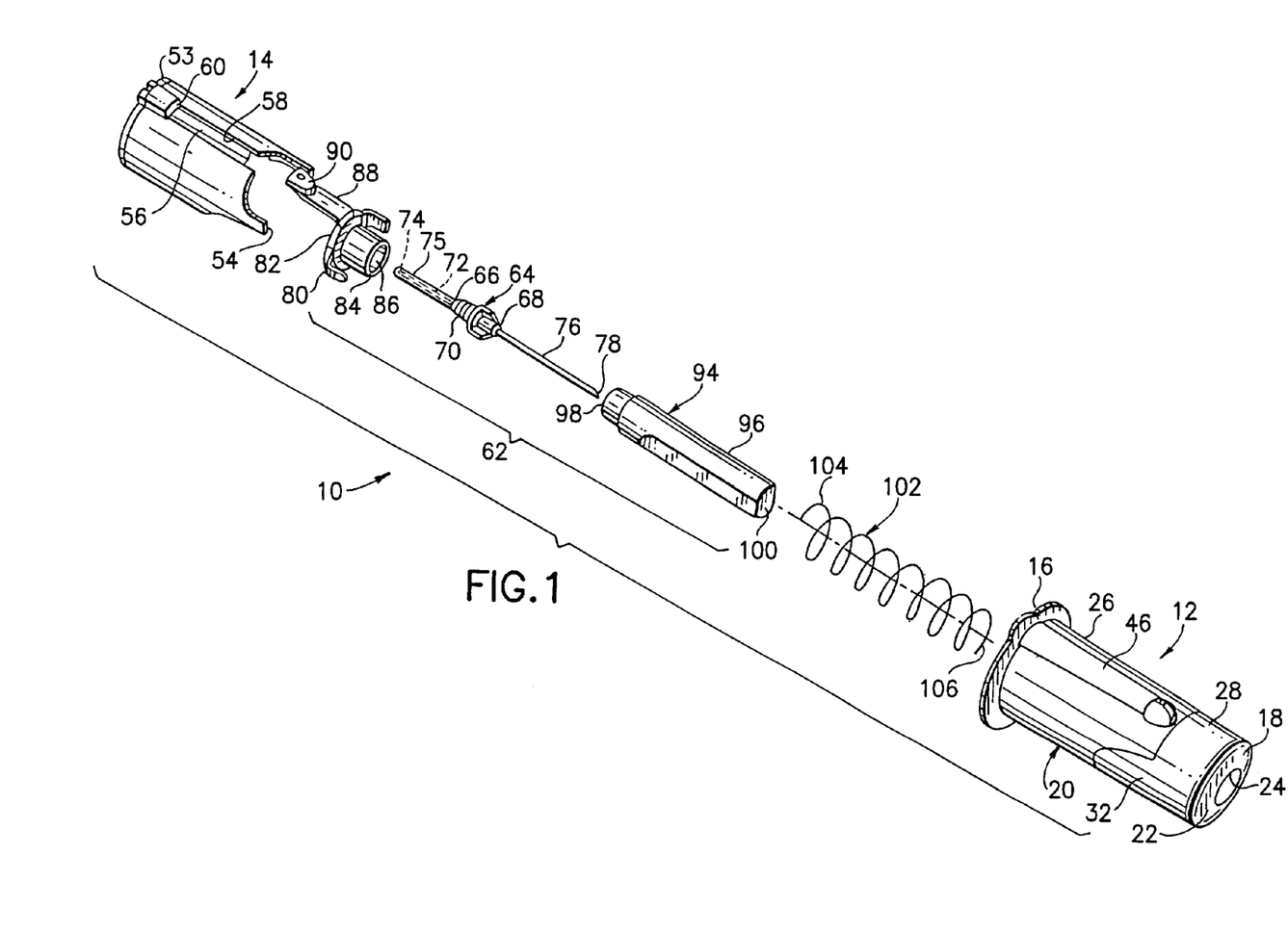
FIG. 1 is an exploded perspective view of a retractable safety needle in accordance with the invention.
Figure 2:
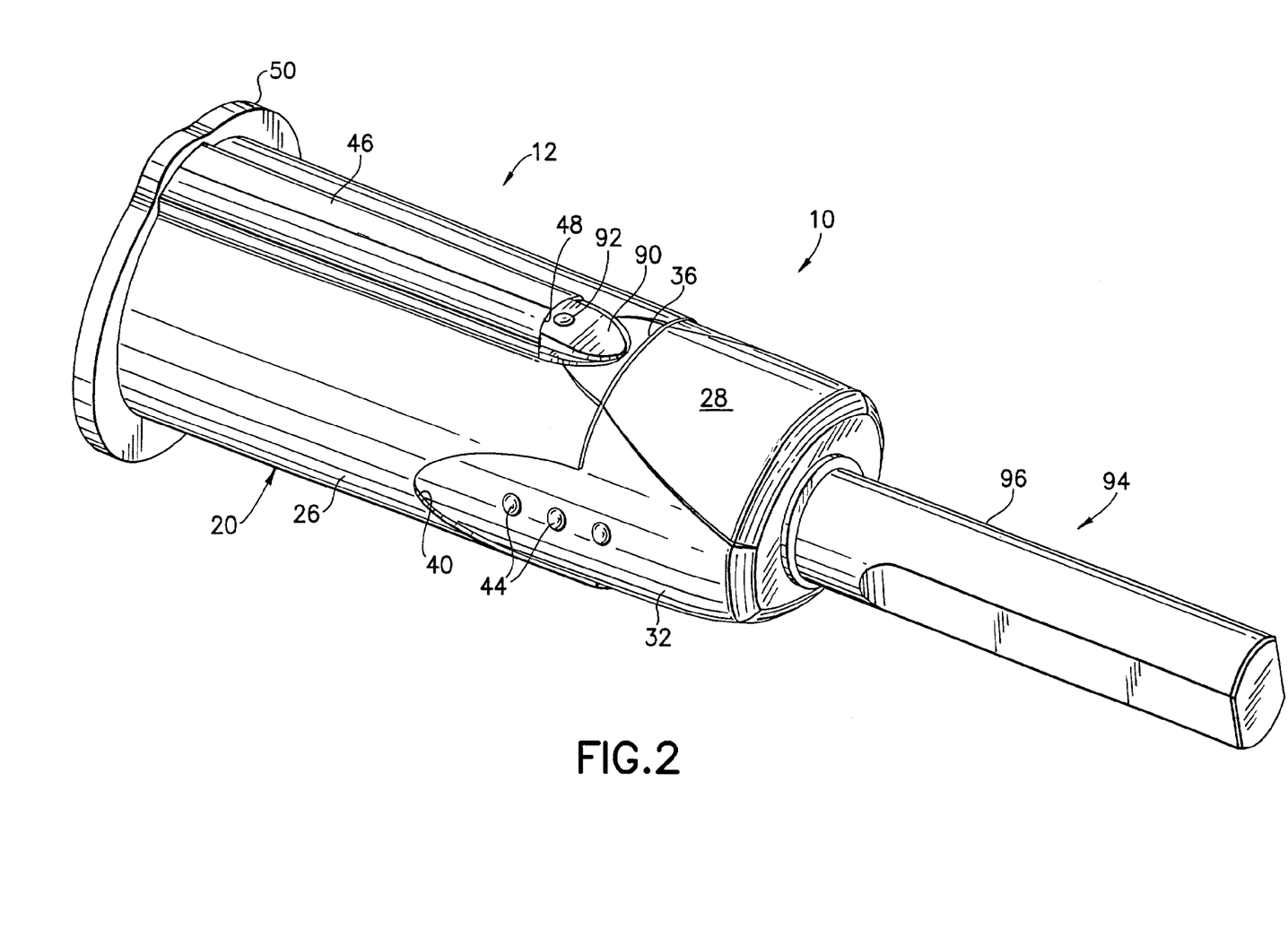
FIG. 2 is a perspective view of the retractable safety needle in its assembled condition.
Figure 3:
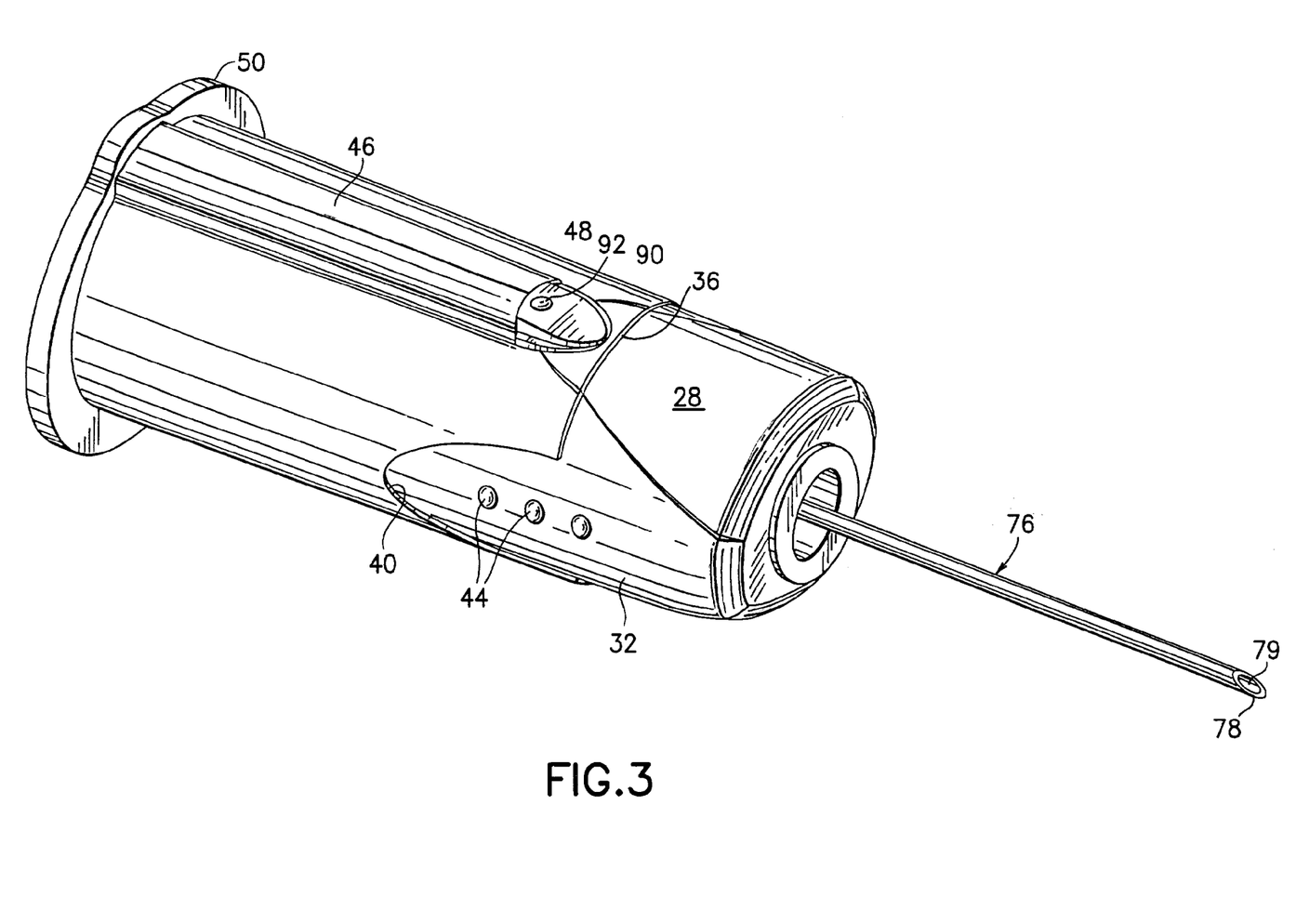
FIG. 3 is a perspective view of the retractable safety needle with the safety shield removed from the distal needle cannula.
Figure 4:
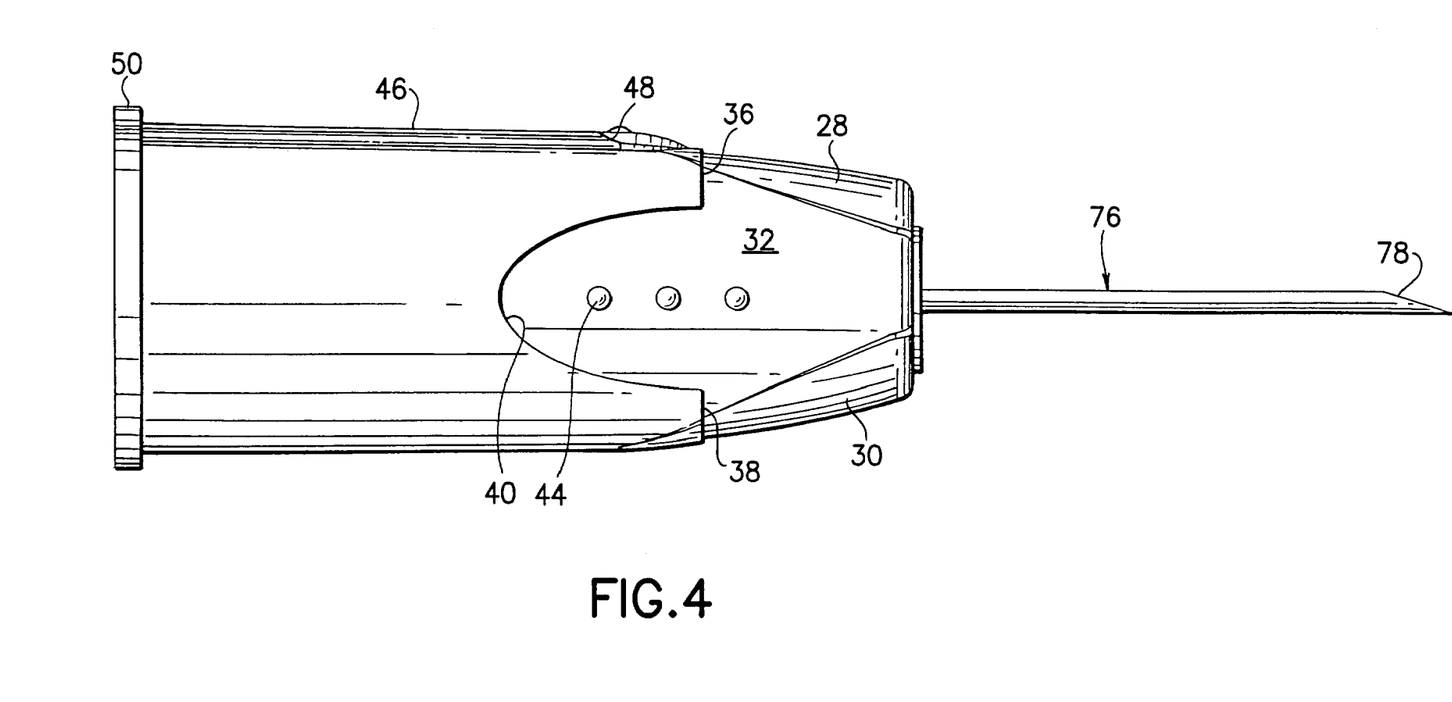
FIG. 4 is a side elevational view of the retractable safety needle.
Figure 5:
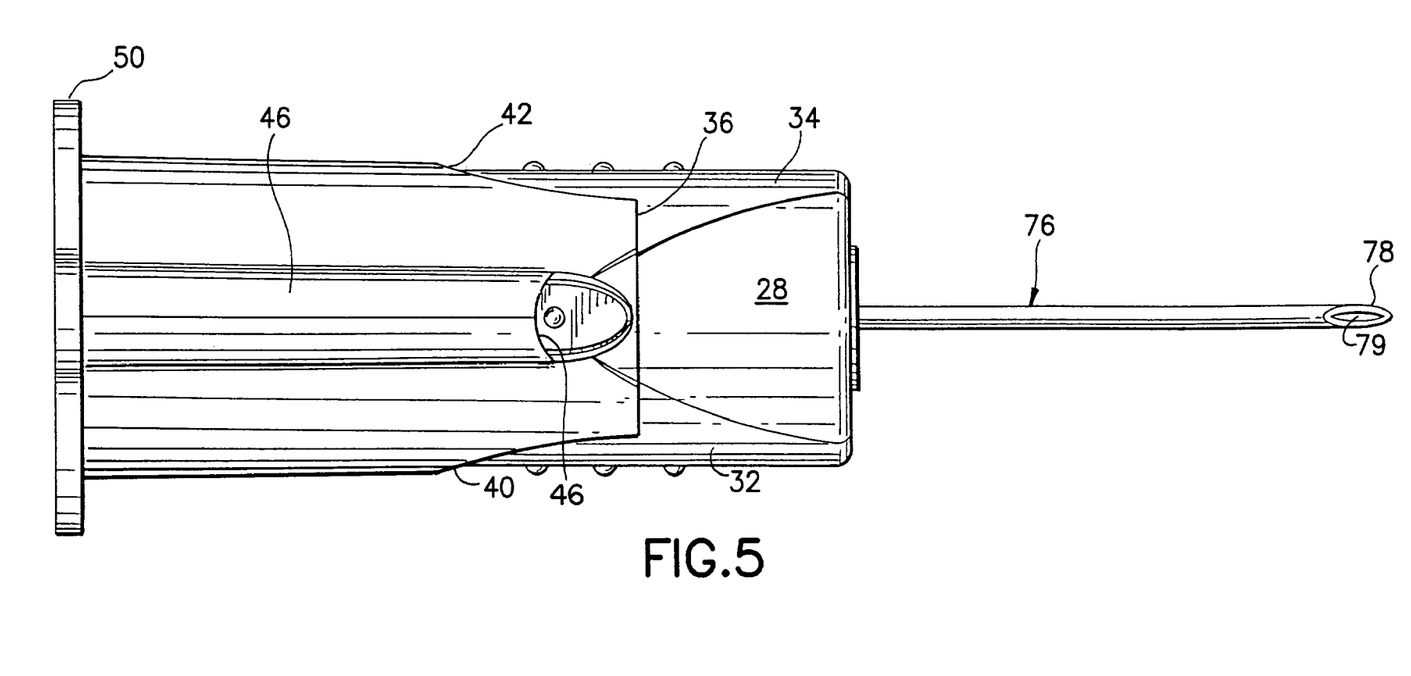
FIG. 5 is a top plan view of the retractable safety needle.
Figure 6:
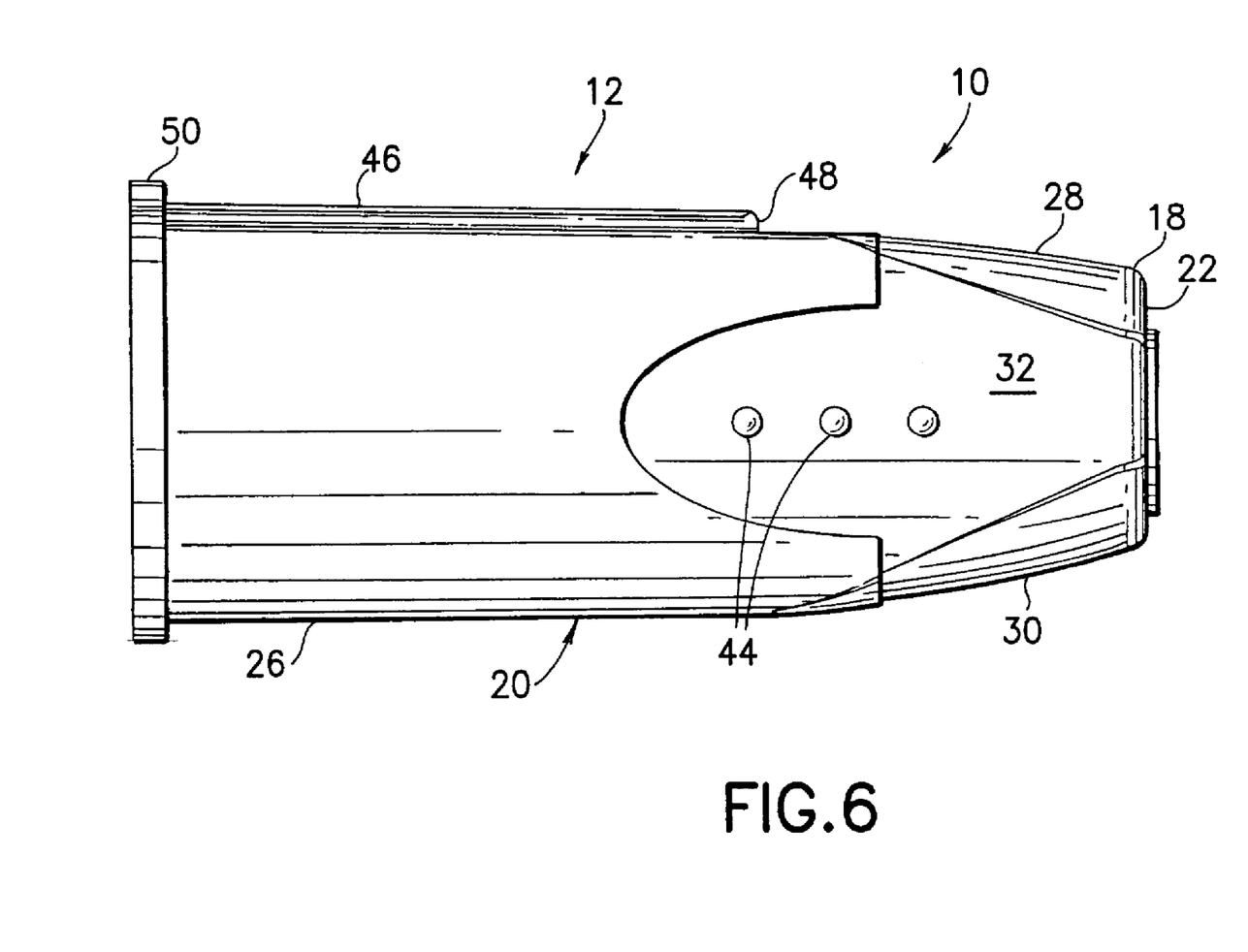
FIG. 6 is a front end view of the retractable safety needle.
Figure 7:
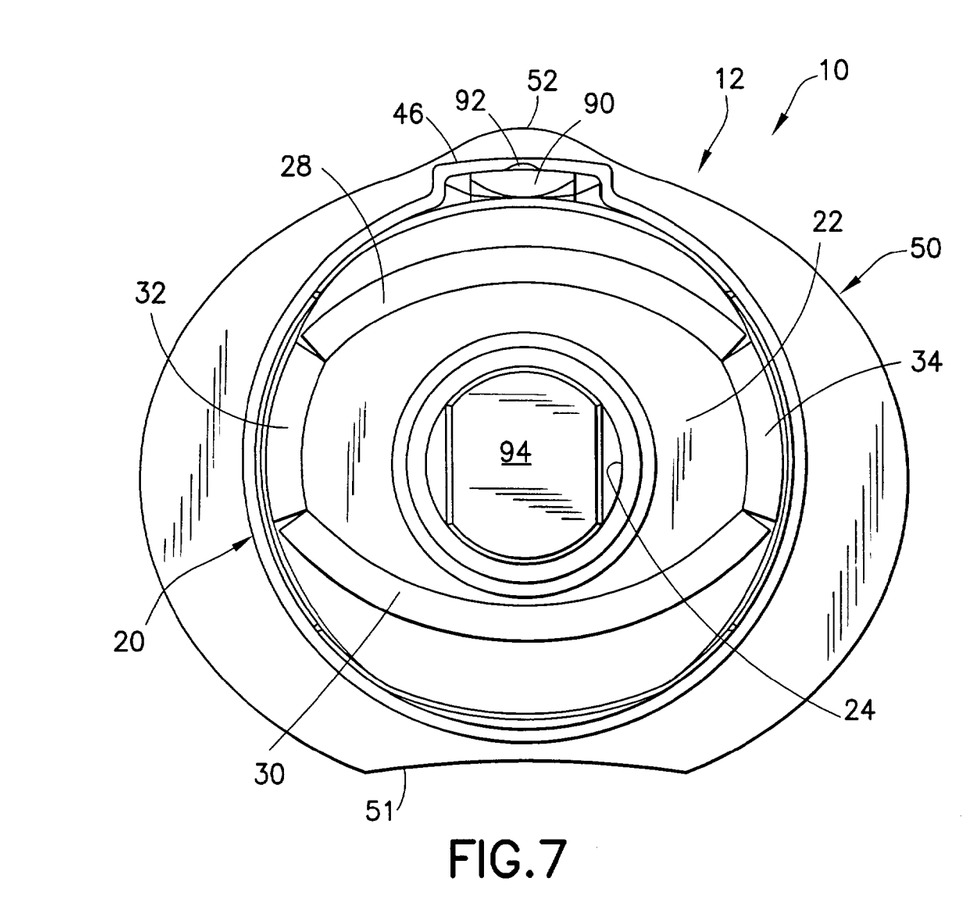
FIG. 7 is a side elevational view of the retractable safety needle with the needle retracted.
Figure 8:
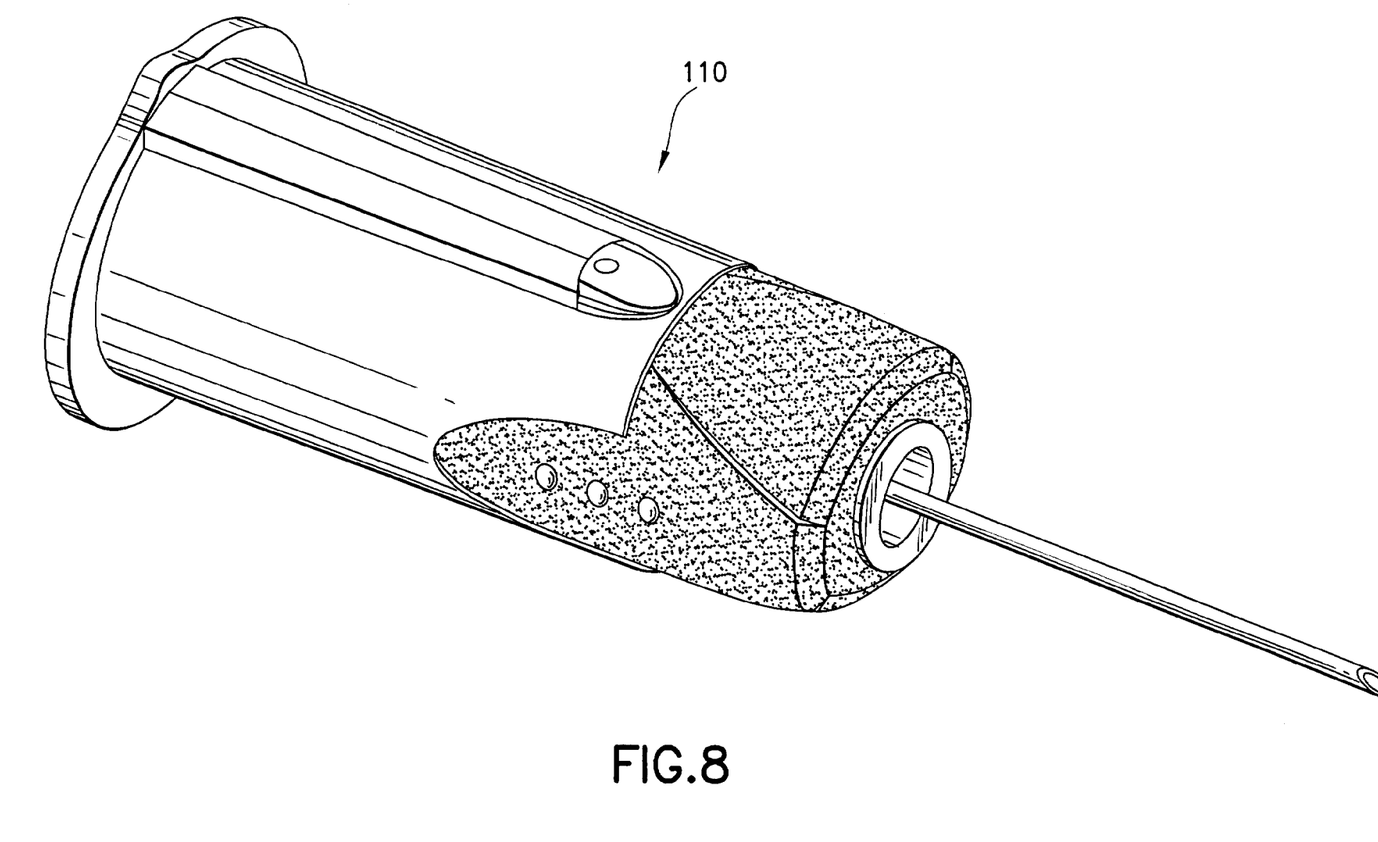
FIG. 8 is a perspective view of an alternate embodiment of the retractable safety needle.

An alternate safety needle assembly is identified generally by the numeral 110 in FIG. 8. Needle assembly 110 is virtually identical to needle assembly 10 described and illustrated above. However, outer surface regions of outer holder 12 forward of boundaries 36, 38, 40 and 42 have a roughened surface texture to facilitate digital manipulation and gripping.

What is claimed is:

1. A retractable safety needle apparatus comprising:
a needle holder having an open proximal end, a distal end and a substantially tubular side wall extending between said ends, a distal end wall extending inwardly from said tubular side wall at said distal end of said needle holder and having a needle aperture extending therethrough, an actuating aperture formed through said side wall of said needle holder;
a needle assembly non-rotatably disposed in said needle holder for axial movement between a proximal position and a distal position, said needle assembly having a distal needle cannula projecting through said needle aperture of said needle holder when said needle assembly is in said distal position, said distal needle cannula being disposed entirely within said needle holder when said needle assembly is in said proximal position;
a spring extending between said distal wall of said needle holder and a portion of said needle assembly for biasing said needle assembly to said proximal position; and
an actuator movable with said needle assembly and deflectable relative to said needle holder, said actuator being releasably engaged in said actuating aperture of said needle holder when said needle assembly is in said distal position, said actuator being selectively deflectable out of engagement with said needle holder permitting said spring to propel said needle assembly to said proximal position.

2. The retractable safety needle apparatus of claim 1, wherein said needle assembly further comprises a proximal needle, said proximal needle being disposed within said needle holder in both said proximal and distal positions of said needle assembly.

3. The retractable safety needle apparatus of claim 1, wherein said side wall of said needle holder includes a cylindrical portion extending from said proximal end of said needle holder to a location in proximity to said actuating aperture, said tubular side wall further including a top panel substantially symmetrical with said actuating aperture and extending from said distal end of said needle holder, a bottom panel opposed to said top panel, said top and bottom panels converging toward one another at locations closer to said distal end of said needle holder.

4. The retractable safety needle apparatus of claim 3, further comprising opposed side panels disposed between the top and bottom panels being recessed relative to said cylindrical portion of said side wall.

5. The retractable safety needle apparatus of claim 4, wherein said side panels extend proximally further than said top and bottom panels and have generally parabolic boundaries with said cylindrical portion of said side wall.

6. The retractable safety needle apparatus of claim 5, wherein said side panels include external surface irregularities for facilitating gripping of said needle holder.

7. The retractable safety needle apparatus of claim 1, wherein said side wall of said needle holder includes an outwardly convex channel extending from said actuating aperture substantially to said proximal end of said needle holder, said channel having a concave inwardly facing surface for slidably receiving said actuator during movement of said needle assembly to said proximal position.

8. The retractable safety needle apparatus of claim 1, wherein said actuator includes an actuator button for projecting releasably into said actuating aperture, said actuating button having at least one surface irregularity for facilitating digital actuation of said actuator button.

9. The retractable safety needle apparatus of claim 1, wherein said actuating aperture and said actuator button each include a pointed distal end.

10. The retractable safety needle apparatus of claim 1, wherein said distal needle cannula has a beveled distal end, said beveled distal end and said actuator being symmetrical about a common plane and facing in substantially a common direction relative to said needle holder.

11. The retractable safety needle apparatus of claim 1, wherein said needle holder includes an outwardly extending flange adjacent said open proximal end, said flange being non-circular and having a minor axis substantially symmetrical with said actuator and a major axis transverse to said minor axis.

12. The retractable safety needle apparatus of claim 1, wherein said flange has a concave recess symmetrical with said minor axis and facing oppositely from said actuator and a convex protrusion symmetrical with said minor axis and facing in a common direction with said actuator.

13. A retractable safety needle apparatus comprising:
a needle holder having an open proximal end, a distal end and a substantially tubular side wall extending between said ends, a distal end wall extending inwardly from said tubular side wall at said distal end of said needle holder and having a needle aperture extending therethrough, portions of said side wall in proximity to said distal end including opposed top and bottom panels converging toward one another at locations closer to the distal end, recessed side panels extending between said top and bottom panels, an actuating aperture formed through said side wall of said needle holder at a location substantially symmetrically aligned with said top panel;
a needle assembly non-rotatably disposed in said needle holder for axial movement between a proximal position and a distal position, said needle assembly having a distal needle cannula with a beveled distal end projecting through said needle aperture of said needle holder when said needle assembly is in said distal position, said distal needle cannula being disposed entirely within said needle holder when said needle assembly is in said proximal position;
a spring extending between said distal wall of said needle holder and a portion of said needle assembly for biasing said needle assembly to said proximal position; and
an actuator movable with said needle assembly and deflectable relative to said needle holder, said actuator having an outwardly extending actuator button symmetrical with said beveled distal end of said distal needle cannula and facing in substantially a common direction as said beveled distal end, said actuator button being releasably engaged in said actuating aperture of said needle holder when said needle assembly is in said distal position, said actuator button being selectively deflectable out of engagement with said needle holder, thereby permitting said spring to propel said needle assembly to said proximal position.

14. The retractable safety needle apparatus of claim 13, wherein said needle assembly further comprises a proximal needle, said proximal needle being disposed within said needle holder in both said proximal and distal positions of said needle assembly.

15. The retractable safety needle apparatus of claim 13, wherein said side wall of said needle holder includes a cylindrical portion extending from said proximal end of said needle holder to said converging top and bottom panels and said recessed side panels.

16. The retractable safety needle apparatus of claim 13, wherein said side wall of said needle holder includes an outwardly convex channel extending from said actuating aperture substantially to said proximal end of said needle holder, said channel having a concave inwardly facing surface for slidably receiving said actuator during movement of said needle assembly to said proximal position.

17. The retractable safety needle apparatus of claim 16, wherein said actuating aperture and said actuator button each include a pointed distal end.

18. The retractable safety needle apparatus of claim 17, wherein said needle holder includes an outwardly extending flange adjacent said open proximal end, said flange being non-circular and having a minor axis substantially symmetrical with said actuator and a major axis transverse to the minor axis.

19. The retractable safety needle apparatus of claim 18, wherein said flange has a concave recess symmetrical with said minor axis and facing oppositely from said actuator and a convex protrusion symmetrical with said minor axis and facing in a common direction with said actuator.

\* \* \* \* \*